(12) United States Patent
Howard et al.

(10) Patent No.: US 12,714,868 B2
(45) Date of Patent: Aug. 25, 2026

(54) PULSED ELECTRIC FIELD ABLATION FOR IMPLANTABLE MEDICAL DEVICES

(71) Applicant: Medtronic, Inc., Minneapolis, MN (US)

(72) Inventors: Brian T. Howard, Minneapolis, MN (US); Timothy G. Laske, Shoreview, MN (US); Alexander J. Hill, Blaine, MN (US); Anthony W. Rorvick, Champlin, MN (US); Robert C. Kowal, Excelsior, MN (US)

(73) Assignee: Medtronic, Inc., Minneapolis, MN (US)

( * ) Notice: Subject to any disclaimer, the term of this patent is extended or adjusted under 35 U.S.C. 154(b) by 430 days.

(21) Appl. No.: 18/194,911

(22) Filed: Apr. 3, 2023

(65) Prior Publication Data

US 2023/0310871 A1 Oct. 5, 2023

Related U.S. Application Data

(60) Provisional application No. 63/327,023, filed on Apr. 4, 2022.

(51) Int. Cl.
*A61N 1/39* (2006.01)
*A61N 1/362* (2006.01)

(52) U.S. Cl.
CPC ............... *A61N 1/39* (2013.01); *A61N 1/362* (2013.01)

(58) Field of Classification Search
CPC .......... A61N 1/39; A61N 1/362; A61N 1/327; A61N 1/3981; A61N 1/39622; A61B 2018/00577; A61B 2018/00613
See application file for complete search history.

(56) References Cited

U.S. PATENT DOCUMENTS 6,968,231 B1 * 11/2005 Silvian ................. A61N 1/3975 607/12
7,620,451 B2 11/2009 Demarais et al.
11,260,237 B1 * 3/2022 Cowan ................. A61N 1/3981
2009/0262979 A1 10/2009 Markowitz et al.
(Continued)

FOREIGN PATENT DOCUMENTS

WO 2005058414 A1 6/2005
WO 2014105964 A1 7/2014

OTHER PUBLICATIONS

Sugrue et al., "Ablation of AF With Pulsed Electric Fields", American College of Cardiology, 2018, 6 pages.
(Continued)

*Primary Examiner* — Paula J Stice
(74) *Attorney, Agent, or Firm* — Michael Best & Friedrich LLP

(57) ABSTRACT

Implantable medical device including a pulsed-voltage generator and one or more implantable electrical leads. In one example, the implantable medical device supports the defibrillator and ablation modalities characterized by different respective sets of waveform parameters, such as the pulse amplitude and width. In some examples, the implantable medical device also supports a pacing modality. The electrodes used for the different modalities are variously selected from a plurality of electrodes located in distal portions of the implantable electrical leads and on the exterior surface of the implantable device box. An electronic controller of the implantable medical device is wirelessly programmable to appropriately control, e.g., in a patient-specific manner, operations of the pulsed-voltage generator and transitions between different modalities. Various examples of the disclosed implantable medical device can beneficially be used to provide to a cardiac patient a greater variety of treatment options without having to replace the implantable medical device.

20 Claims, 11 Drawing Sheets

(56) References Cited

U.S. PATENT DOCUMENTS

| | | | | |
|---|---|---|---|---|
| 2018/0264274 | A1* | 9/2018 | Haasl | A61N 1/059 |
| 2019/0054297 | A1 | 2/2019 | Zhang et al. | |
| 2019/0175111 | A1 | 6/2019 | Genereux et al. | |
| 2019/0216525 | A1 | 7/2019 | Stewart et al. | |
| 2020/0046423 | A1 | 2/2020 | Viswanathan et al. | |
| 2020/0155845 | A1* | 5/2020 | Bonner | A61N 1/37518 |
| 2020/0155863 | A1 | 5/2020 | Min | |
| 2021/0260391 | A1 | 8/2021 | Kaiser et al. | |
| 2021/0370076 | A1 | 12/2021 | Ecker et al. | |
| 2022/0096832 | A1 | 3/2022 | Peterson | |

OTHER PUBLICATIONS

Varghese et al., "Low-energy defibrillation with nanosecond electric shocks", Cardiovascular Research, 2017, vol. 113, Issue 14, pp. 1789-1797.

Pakhomov, "Low energy Defibrillation with Nanosecond Pulsed Electric Field", National Institute of Health, Abstract, 2015, 3 pages.

Khatoon et al., "Bacterial biofilm formation on implantable devices and approaches to its treatment and prevention", University of Ottawa Canada, 2018 <https://www.ncbi.nlm.nih.gov/pmc/articles/PMC6312881/>, 19 pages.

Grahl et al., "Killing of Microorganisms by pulsed electric fields", Appl. Microbiol Biotechnol., 1996, vol. 45, No. 1-2, pp. 148-157.

Golberg et al., "Pulsed Electric Fields for Burn Wound Disinfection in a Murine Model", J Burn Care Res., 2015, vol. 36, No. 1, pp. 7-13.

International Search Report and Written Opinion for Application No. PCT/US2023/065271 dated Jun. 23, 2023 (14 pages).

Sale et al., "Effects of High Electric Fields on Microorganisms" Biochimica et Biophysica ACTA, 1967, vol. 148, pp. 781-788.

International Preliminary Report on Patentability for Application No. PCT/US2023/065271 dated Oct. 17, 2024 (8 pages).

* cited by examiner

Legend:
1 —— Voltage
2 – – – Pulse Width
3 –·–·– Pulse Count
4 ------- Frequency Of Treatment

PULSED ELECTRIC FIELD ABLATION FOR IMPLANTABLE MEDICAL DEVICES

CROSS-REFERENCE TO RELATED APPLICATION

This application claims the benefit of U.S. Provisional Patent Application No. 63/327,023, filed 4 Apr. 2022, and entitled "INCORPORATION OF PULSED ELECTRIC FIELD ABLATION INTO IMPLANTABLE MEDICAL DEVICES."

FIELD

This application relates generally to implantable medical devices and heart disease treatment.

BACKGROUND

An implantable medical device is placed in the human body during surgery or other clinical intervention to replace a missing biological structure, support a damaged biological structure, or enhance an existing biological structure or function. Implantable medical devices are man-made devices, in contrast to transplants, which are typically natural organs transplanted to a human body from another biological body. Some implantable medical devices contain electrical circuits.

As defined by the U.S. Food and Drug Administration, an active medical device is a "medical device relying for its functioning on a source of electrical energy or any source of power other than that directly generated by the human body or gravity." An implantable medical device is a "medical device which is intended to be totally or partially introduced, surgically or medically, into the human body or by medical intervention into a natural orifice, and which is intended to remain after the procedure." Various active implantable medical devices may remain in the body for several days, weeks, months, or years.

SUMMARY

Disclosed herein are, among other things, various examples, aspects, features, and embodiments of an implantable medical device including a pulsed-voltage generator and one or more implantable electrical leads. In one example, the implantable medical device supports the defibrillator and ablation modalities characterized by different respective sets of waveform parameters, such as the pulse amplitude and width. In some examples, the ablation modality is supported at different selectable strength levels, e.g., suitable for irreversible ablation, reversible electroporation, and premature ventricular contractions (PVC) treatments, respectively. In some examples, the implantable medical device also supports a pacing modality. The electrodes used for the different modalities are variously selected from a plurality of electrodes located in distal portions of the implantable electrical leads and on the exterior surface of the implantable device box. An electronic controller of the implantable medical device is wirelessly programmable to appropriately control, e.g., in a patient-specific manner, various operations of the pulsed-voltage generator and transitions between different modalities. Various examples of the disclosed implantable medical device can beneficially be used to provide to a cardiac patient a greater variety of treatment options without having to replace the implantable medical device.

One example provides an active implantable medical device. The device includes a plurality of electrodes, including a first electrode and a second electrode, and an electrical circuit in an interior portion of an implantable device box. The electrical circuit is electrically connectable to the plurality of electrodes to apply thereto electrical pulses according to a first modality and according to a different second modality. The device also includes a first electrical lead having a proximal end connectable to the electrical circuit and further having a distal portion implantable into a heart. The distal portion includes the first electrode and the second electrode. The electrical circuit is configured to apply a defibrillation pulse to the first electrode in the first modality and to apply an ablation pulse to the second electrode in the second modality. The defibrillation pulse and the ablation pulse are different in at least one of a pulse amplitude and a pulse width.

Another example provides a medical system. The medical system includes an active implantable medical device including a first wireless transceiver, a programmer head including a second wireless transceiver, and an electronic programmer connected to the programmer head. The first and second wireless transceivers are configured to wirelessly transmit data therebetween. The device includes a plurality of electrodes, including a first electrode and a second electrode, and an electrical circuit in an interior portion of an implantable device box. The electrical circuit is electrically connectable to the plurality of electrodes to apply thereto electrical pulses according to a first modality and according to a different second modality. The device also includes a first electrical lead having a proximal end connectable to the electrical circuit and further having a distal portion implantable into a heart. The distal portion includes the first electrode and the second electrode. The electrical circuit is configured to apply a defibrillation pulse to the first electrode in the first modality and to apply an ablation pulse to the second electrode in the second modality. The defibrillation pulse and the ablation pulse are different in at least one of a pulse amplitude and a pulse width.

DETAILED DESCRIPTION

Figure 1:
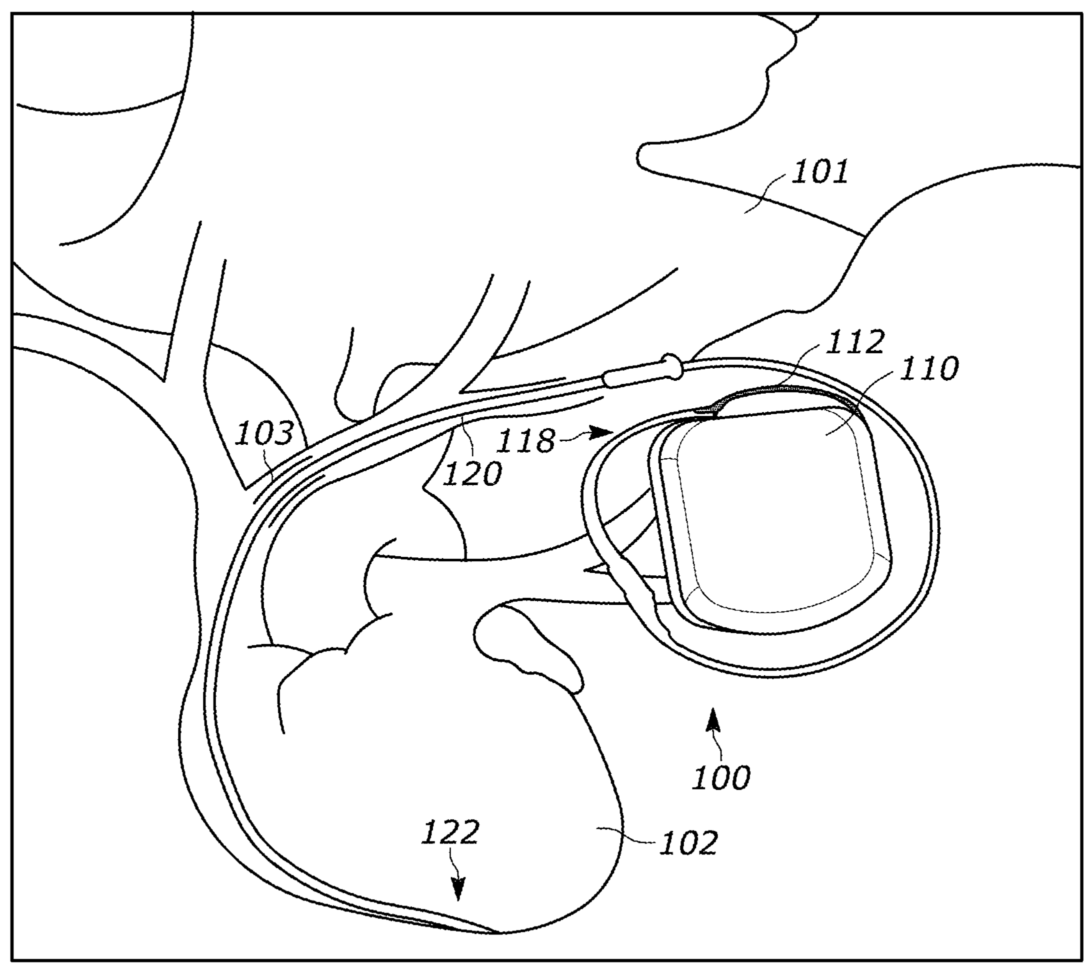
FIG. 1 is a pictorial diagram illustrating an active implantable medical device according to one example.

Pulsed field ablation (PFA) involves the application of pulsed electric fields (PEF), which may reversibly or irreversibly destabilize cell membranes through electro-permeabilization, but generally do not affect the structural integrity of the tissue components, including the acellular cardiac extracellular matrix. The nature of PFA allows for very brief periods of therapeutic energy delivery, e.g., on the order of tens of milliseconds in duration. In at least some examples, PFA does not cause collateral damage to non-targeted tissue as frequently or severely as thermal ablation techniques. Additionally, pharmacologic agents may be preferentially introduced into the cells of targeted tissue that are exposed to PEF via reversible membrane permeabilization.

Catheters inserted and navigated through blood vessels are used to probe and treat a variety of medical conditions. For example, cardiac arrythmias are treated by inserting a catheter into a blood vessel and guiding the end thereof to the heart. The end of the catheter typically has electrodes for applying electrical energy. At least some of the electrodes can be used to detect electrical activity in surrounding tissues and/or to deliver PEF treatment to the tissue.

For illustration purposes and without any implied limitations, some example embodiments are described herein below in reference to an implantable cardiac defibrillator (ICD). However, various embodiments are not so limited. Based on the provided description, a person of ordinary skill in the pertinent art will be able to make and use other embodiments without any undue experimentation. In some examples, the corresponding implantable medical device is selected from the group consisting of a sensor, a cardiac pacemaker, a defibrillator, and a stimulator.

An ICD is a device implanted into a patient to provide electrical stimulus to the heart to cause the heart muscles to restore a substantially normal heartbeat. ICDs are useful for treating patients exhibiting sustained ventricular tachycardias or fibrillation. In some examples, an ICD plays a role in preventing cardiac arrest in the host patient. Various ICDs or similar devices are used to terminate ventricular arrhythmias and/or atrial arrhythmias.

Some ICDs are designed to provide a dual function which includes the ability to serve as a pacemaker. When activated, the pacemaker feature stimulates the heart to beat either transiently or continuously in instances of the observed heart rate being too slow compared to a nominally normal heart rate. The defibrillator feature is used to deliver an occasional electrical signal to the heart, whereas the pacemaker feature is used to deliver a regularly occurring electrical stimulus to the heart. In some descriptions, the electrical stimulus to the heart by a pacemaker is referred to as pacing or cardiac resynchronization therapy (CRT).

As used herein, various instances of the terms “pulse,” “pulsed signal,” and “pulsed electric field” refer to a single pulse or to a train of pulses. In some instances, a single pulse or a train of pulses vary in amplitude over a time interval during which such single pulse or train of pulses exists.

FIG. 1 is a pictorial diagram illustrating an active implantable medical device 100 according to one example. In the example shown, the medical device 100 is an ICD that has been implanted into a living human body 101. Depending on the specific medical condition of the body 101, the ICD 100 can, for example, operate to: (i) correct a cardiac arrhythmia, such as a heart rate or rhythm that is irregular, too fast (tachycardia), or too slow (bradycardia); (ii) prevent sudden cardiac arrest; and (iii) gather data about the function of a heart 102 in the body 101, e.g., to help the corresponding healthcare provider make treatment recommendations. The ICD 100 is different from a pacemaker (which is another example of an active implantable medical device) in that a pacemaker consistently maintains a normal heart rate, whereas the ICD 100 operates to monitor the heart rate and intervene only when needed. However, in some examples, the ICD 100 implements functions of a pacemaker as explained above.

In various examples, the ICD 100 comprises a device box 110 and one, two, or three electrical leads 120. The device box 110 typically includes a pulse generator, a device battery, and additional electronic circuits (not explicitly shown in FIG. 1, e.g., see FIG. 3). The electrical leads 120 typically pass through a vein 103 (usually the large vein under the left or right collarbone) into the heart 102. At a proximal end 118, each of the electrical leads 120 is connected to a respective electrical terminal on a connector block 112 of the device box 110. At a distal end 122, which is typically attached to the heart muscle, each of the electrical leads 120 typically has a respective electrode electrically connected thereto. In some examples, the electrical leads 120 are made of fine, flexible wires covered with plastic or silicone rubber. The device battery is typically a lithium battery capable of lasting up to approximately 5-7 years under average operating conditions.

In various examples, there are typically two stages to implanting the ICD 100 into the body 101. First, the electrical leads 120 are inserted. Second, the device box 110 is implanted. To insert the electrical leads 120, a surgeon makes a small incision, typically under the left collarbone. The electrical leads 120 are then fed through the vein 103 into the heart 102. When a single electrical lead 120 is inserted, the distal end 122 of the single electrical lead is placed in the right ventricle of the heart 102. When two electrical leads 120 are inserted, the distal end 122 of one is placed in the right ventricle and the distal end 122 of the other is placed in the right atrium of the heart 102. If a third electrical lead 120 is used, then the distal end 122 of the third electrical lead is typically placed in the left ventricle of the heart 102. Various example geometric configurations of the electrical leads 120 are described in more detail below in reference to FIGS. 4-7. The position of the electrical lead(s) 120 is typically checked on an X-ray screen. When the electrical leads 120 are in the right place, the electrical leads are secured with one or more stitches. After the electrical leads 120 have been placed and tested, the surgeon makes a small space (typically referred to as a “pocket”) for the device box 110 under the muscle or skin, for example, below the left collarbone. The surgeon then connects the proximal ends 118 of the electrical leads 120 to the respective electrical terminals on the connector block 112 and places the device box 110 into the pocket. After the requisite testing of certain functions of the ICD 100 in the pocket, the wound is closed.

Figure 2:
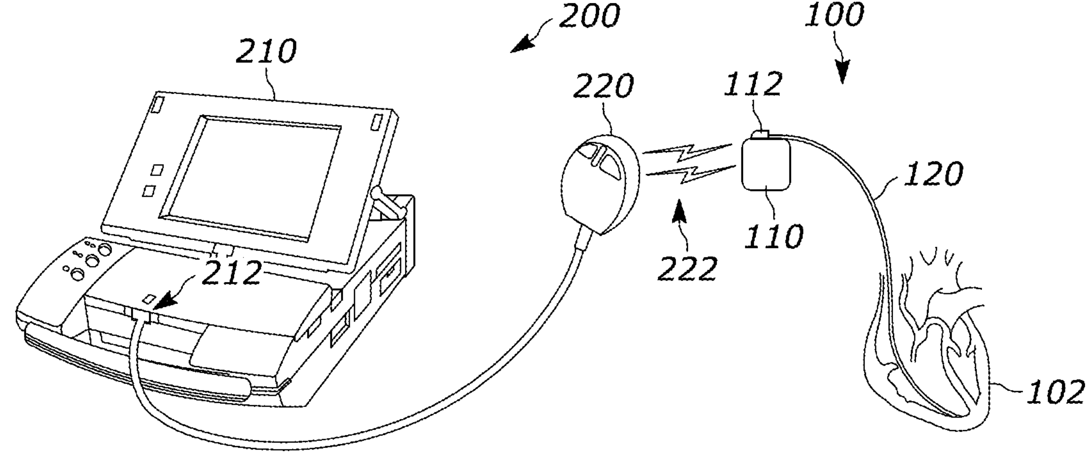
FIG. 2 is a block diagram illustrating a medical system used to program and interrogate the active implantable medical device of FIG. 1 according to various examples.

FIG. 2 is a block diagram illustrating a medical system 200 used to program and interrogate the ICD 100 according to various examples. The ICD 100 typically has a set of programmable features. In some examples, the ICD 100 operates to categorize the heart rate as normal, too fast, or too slow by measuring cardiac RR intervals. An RR interval is the time elapsed between two successive R waves of the QRS signal on the electrocardiogram, and its reciprocal is the heart rate. When the ICD 100 detects a threshold number of abnormal RR intervals within a fixed time duration, the internal processor thereof uses a programmed algorithm to decide on the type of intervention, such as anti-tachycardia or anti-bradycardia pacing, synchronized cardioversion, or internal defibrillation. Detailed diagnostic data concerning intracardiac electrograms and event markers are stored in the memory of the ICD 100 and can be retrieved for analyses.

In some examples, programming and interrogation of the ICD 100 are performed using an electronic programmer 210 connected to a programmer head 220. Electronic programmer 210 comprises a computer and an input/output (I/O) interface 212 for connecting the programmer head 220 thereto. The computer runs a program code and communicates with the programmer head 220 via the I/O interface 212. The programmer head 220 includes a wireless transceiver. When the programmer head 220 is placed over a skin portion of the body 101 adjacent to the device box 110 of the ICD 100, the wireless transceiver of the ICD wirelessly sends and receives data-modulated signals 222 to/from a corresponding wireless transceiver located in the device box 110. In various examples, the data-modulated signals 222 are used to monitor the amount of battery life remaining, check and/or change the settings of the ICD 100, ensure that various components of the ICD 100 are functioning properly, download data stored in the memory of the ICD 100 for evaluation, and upload data and program code to the ICD 100 to make software updates and/or configuration changes.

Figure 3:
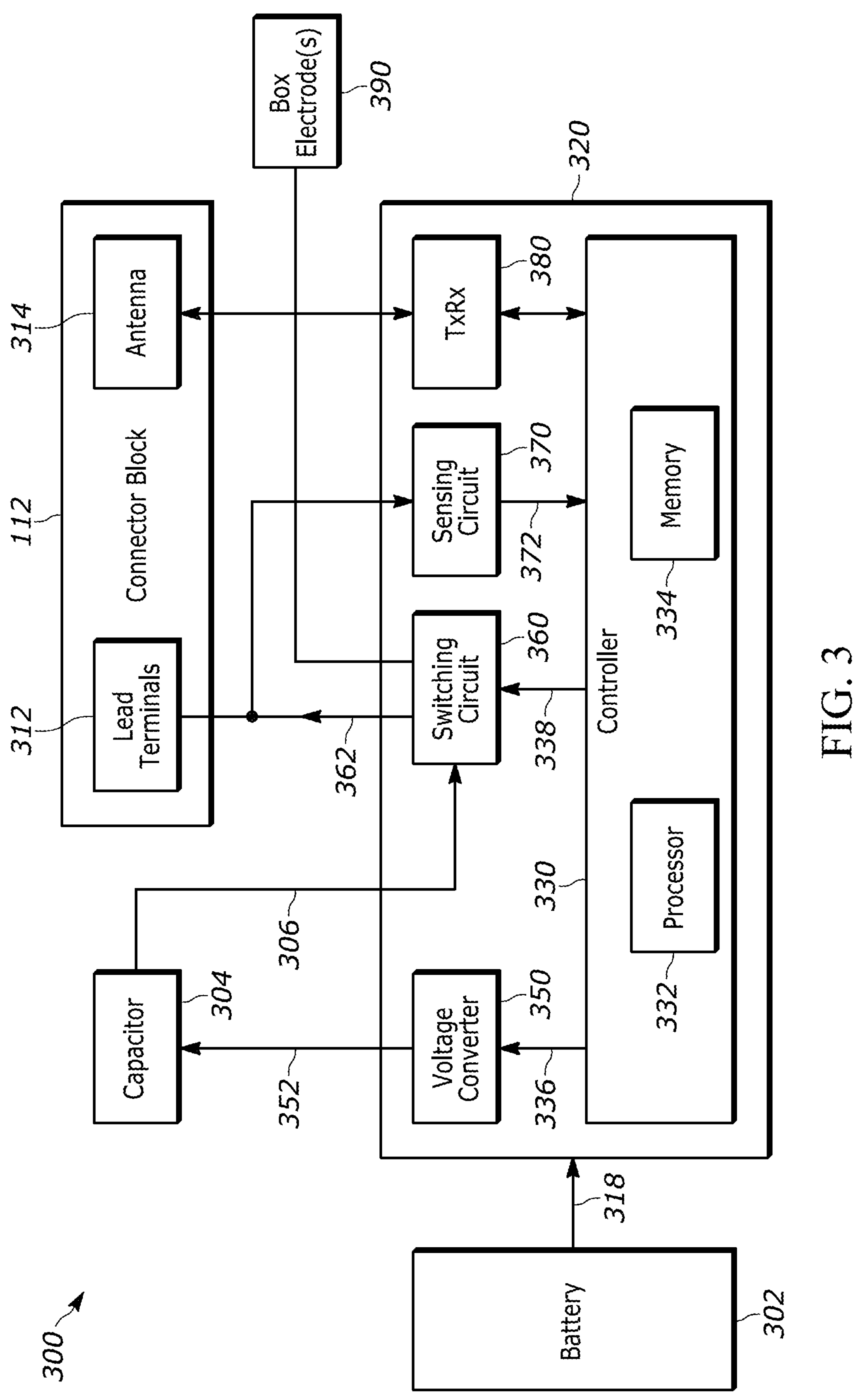
FIG. 3 is block diagram illustrating an electrical circuit used in the implantable medical device of FIG. 1 according to various examples.

FIG. 3 is block diagram illustrating an electrical circuit 300 located at the device box 110 according to various examples. Some parts of the circuit 300 are located inside the device box 110. Some other parts of the circuit 300 are located outside the device box 110, e.g., near or on the exterior surface thereof. In the example shown, the circuit 300 includes a battery 302, a capacitor 304, the connector block 112 (also see FIGS. 1-2), a printed circuit board (PCB) 320, and one or more box electrodes 390. The battery 302 is connected to provide an electrical power supply 318 to the various circuits located on the PCB 320. The connector block 112 typically protrudes out of the device box 110 and includes lead terminals 312 to which the electrical leads 120 are connected (also see FIGS. 1-2). The connector block 310 also includes an antenna 314 for wirelessly communicating with the programmer head 220 and a suture anchor (not explicitly shown in FIG. 3) for securing the device box 110 in the pocket of the body 101. The battery 302, the capacitor 304, and the PCB 320 are typically located inside the device box 110. In some examples, the box electrode(s) 390 is (are) located near or on the exterior surface of the device box 110. In some other examples, the device box 110 is made of an electrically conducting material (e.g., a metal or metal alloy) and is electrically connected to the switching circuit 360 to serve as the box electrode 390.

The PCB 320 has an electronic controller 330 attached and electrically connected thereto. The electronic controller includes a processor 332, a memory 334, and other circuits for controlling various functions of the circuit 300. In some examples, the processor 332 operates to execute program code having encoded therein various algorithms and instructions for operating the circuit 300. The memory 334 is used to store the program code and further store diagnostic data representing intracardiac electrograms and event markers, configuration and control parameters, device management information, and other data pertinent to the functions of the ICD 100. In some examples, portions of algorithms are implemented in hardware.

The PCB 320 also has a voltage converter 350, a switching circuit 360, a sensing circuit 370, and a wireless transceiver (TxRx) 380 attached and electrically connected thereto. In operation, the voltage converter 350 converts a low voltage of the electrical power supply 318 into a high voltage 352 that is used to charge the capacitor 304. The low voltage of the electrical power supply 318 is typically in the range between 2.5 V and 3.3 V. The magnitude of the high voltage 352 is controlled via a control signal 336 generated by the electronic controller 330. In various examples, the high voltage 352 is in the range between 10 V and 10 kV.

The switching circuit 360 operates to generate voltage or current pulses 362 using a high-voltage input 306 received from the capacitor 304. The switching performed in the switching circuit 360 is controlled via a control signal 338 generated by the electronic controller 330. In various examples, the control signal 338 controls the waveform(s) of the generated voltage or current pulses 362 and determines to which of the lead terminals 312 the pulses are applied. In various examples, the switching circuit 360 is controlled, via the control signal 338, to generate a pulse waveform characterized by selected values of various parameters. Specific sets of values for such parameters are selected to apply various types of treatment to the heart 102. Various waveform parameters that can be controlled via the control signal 338 include but are not limited to: (i) pulse polarity, e.g., unipolar (monophasic) or bipolar (biphasic); (ii) voltage amplitude; (iii) pulse duration, e.g., from nanoseconds to milliseconds; (iv) interphase interval; (v) inter-pulse interval; (vi) the number of pulses in a pulse sequence; and (vii) the number of pulse sequences in a procedure.

The sensing circuit 370 is connected to the lead terminals 312 to sense electrical (e.g., electrocardiogram) signals delivered thereto via the electrical leads 120. The sensing circuit 370 is electrically isolated from the lead terminals 312 when the voltage or current pulses 362 are being applied thereto by the switching circuit 360. The sensing circuit 370 typically includes one or more sense amplifiers able to respond to varying cardiac signals by changing the sensing threshold, e.g., through an autogain feature thereof, on a fast time scale, e.g., on a beat-to-beat basis. The amplified signals generated by the sense amplifiers are digitized to generate digital signals 372, which are directed to the electronic controller 330 for processing and analysis. In some examples, such processing and analysis are directed at detecting various episodes of cardiac arrhythmia as indicated above.

The wireless transceiver 380 is connected to the antenna 314. The wireless transceiver 380 operates to generate data-modulated radio-frequency (RF) signals based on the data received from the electronic controller 330 and to apply the generated RF signals to the antenna 314 for transmission to the programmer head 220 (FIG. 2). The wireless transceiver 380 also operates to: (i) receive, through the antenna 314, data-modulated RF signals transmitted by the programmer head 220; (ii) demodulate the received data-modulated RF signals to recover the corresponding data; and (iii) direct the recovered data to the electronic controller 330. In various examples, the wireless transceiver 380 is used to transmit telemetry, send and receive control signals, and perform programming and configuration updates.

Figure 4:
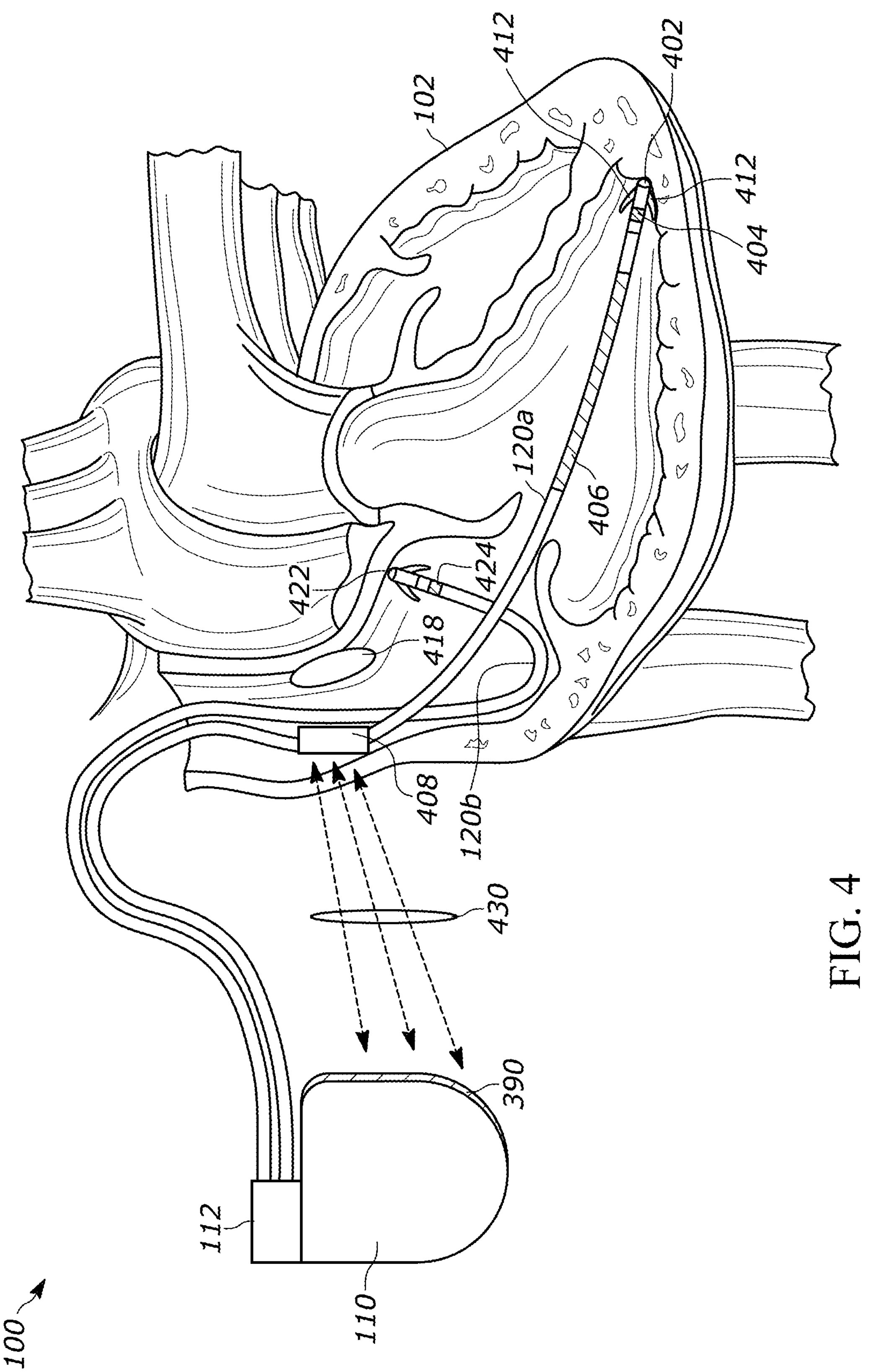
FIG. 4 is a block diagram illustrating a geometric configuration of the implantable medical device of FIG. 1 with respect to the patient heart according to one example.
Figure 5:
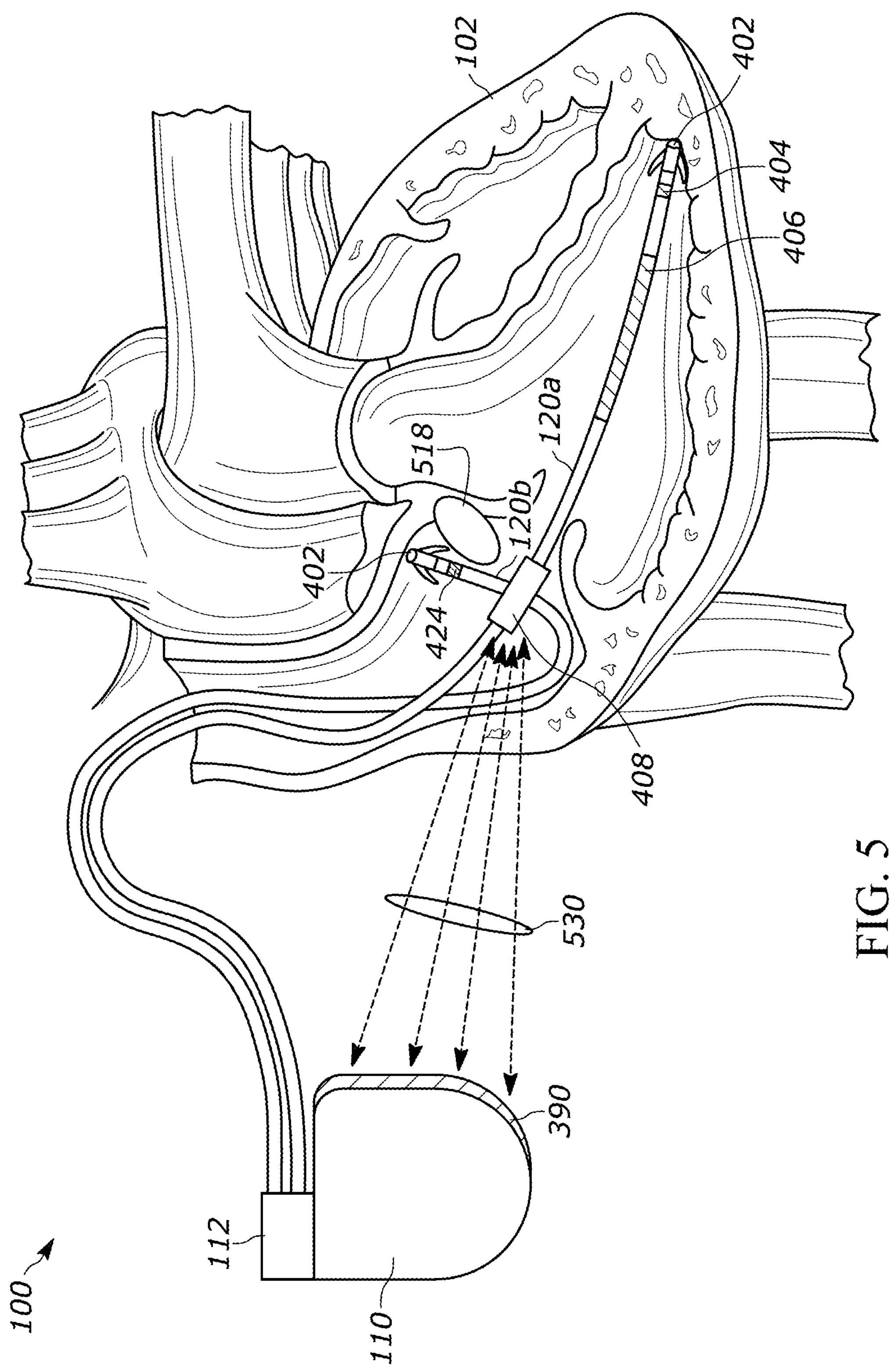
FIG. 5 is a block diagram illustrating a geometric configuration of the implantable medical device of FIG. 1 with respect to the patient heart according to another example.
Figure 7:
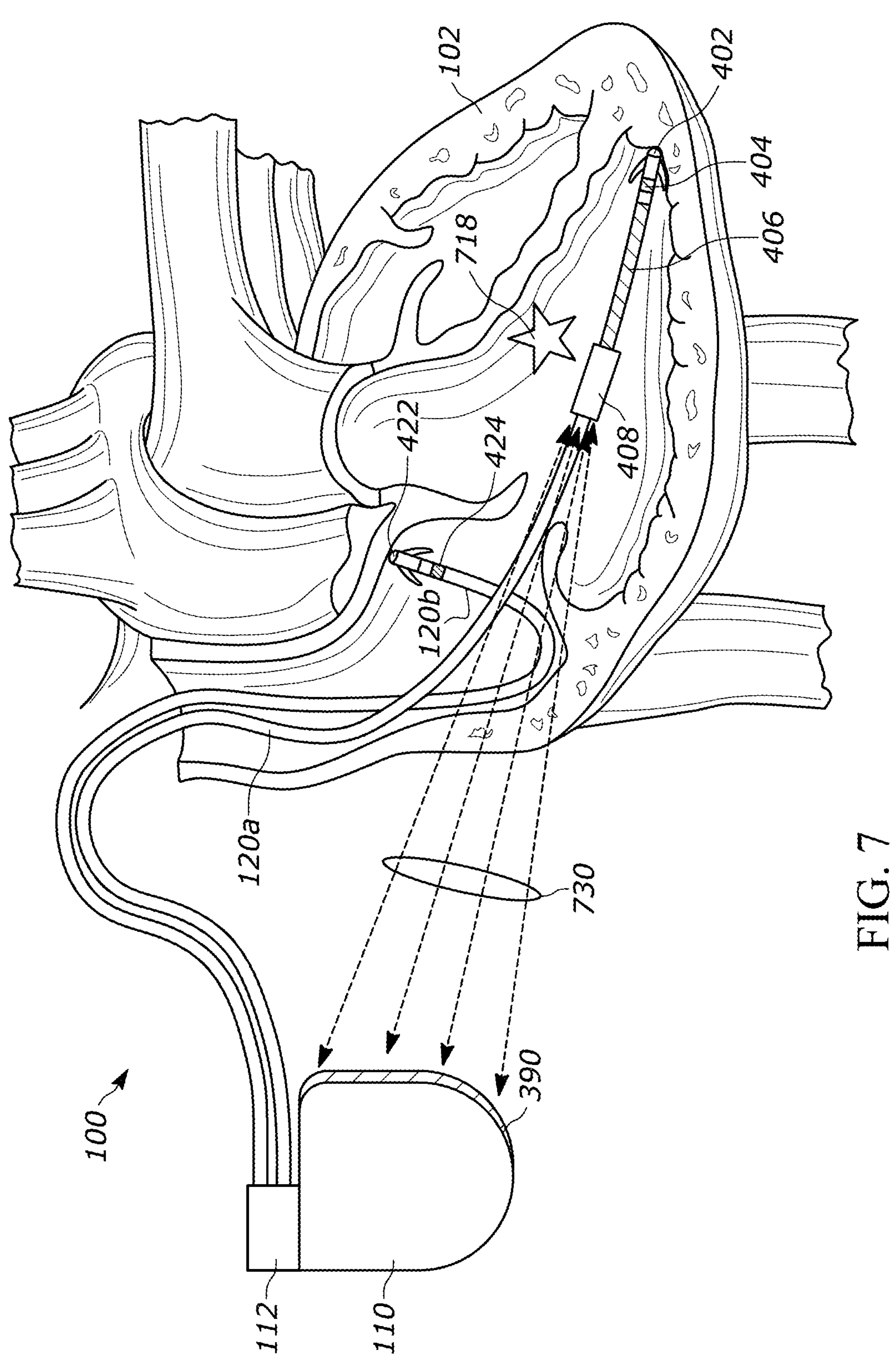
FIG. 7 is a block diagram illustrating a geometric configuration of the implantable medical device of FIG. 1 with respect to the patient heart according to yet another example.

The box electrode 390 is configured to be used in a PFA treatment. For example, in some electrical configurations, the box electrode 390 serves as a counter electrode to an electrode connected, via the corresponding electrical lead 120, to one of the lead terminals 312. In such electrical configurations, a voltage pulse applied between the box electrode 390 and the corresponding electrode connected to one of the lead terminals 312 causes a corresponding electrical current to flow therebetween, e.g., as indicated in FIGS. 4-5 and 7. This electrical current flows through at least some of the tissues for which the PFA treatment is intended. In various examples, the box electrode(s) 390 have various geometric shapes/configurations suitable for delivering the intended PFA treatment. Such shapes/configurations include but are not limited to: (i) a flat ribbon electrode; (ii) a paddle electrode; (iii) a braided or woven electrode; (iv) a mesh electrode; (v) a segmented electrode; (vi) a directional electrode; (vii) a patch electrode, and (vii) a coil electrode. In some examples, geometric shapes/configurations for the box electrode(s) 390 are selected based on the type of the corresponding implantable medical device 100, the geometry of the corresponding device box 110, the anatomy of the corresponding pocket, and the type(s) of treatment delivered by the device.

In one example, the circuit 300 is configured to support three different modalities. A first modality is a defibrillator modality in which the switching circuit 360 operates to apply to the appropriate ones of the lead terminals 312 one or more defibrillation pulses with an amplitude between 200 V and 1 kV. An individual defibrillation pulse typically has a duration in the range between 5 ms and 10 ms. A second modality is a PFA modality in which the switching circuit 360 operates to apply to the appropriate ones of the lead terminals 312 and/or the box electrode(s) 390 a train of PFA pulses. Example parameters for the PFA modality are: (i) a pulse train including 10-100 pulses; (ii) a pulse width in a microsecond to millisecond range; and (iii) a pulse repetition frequency of 1-10 Hz. The amplitude of PFA pulses is selected based on the configuration of the corresponding delivery electrodes so that an electric field in the range between 500 V/cm and 3 kV/cm is created in the target tissue. For example, electroporation is dependent on the cellular geometry and orientation of the electric field with respect to the cell because the local current density creates a local electric field and voltage across each tissue cell in proportion to the cell size measured in the axial direction of the electrical current. In some representative examples, the amplitude of the pulses used for the PFA modality is in the range between 500 V and 5 kV. A third modality is a pacemaker modality in which the switching circuit 360 operates to apply to the appropriate ones of the lead terminals 312 a train of pacemaker pulses. In some examples, an individual pacemaker pulse has an amplitude in the range between 1 V and 15 V and a pulse width in the range between 0.5 ms and 25 ms. The pulse repetition rate in the pacemaker pulse train is typically in the range between 0.5 Hz and 5 Hz. In some examples, the circuit 300 supports only the first and second modalities but does not support the third modality.

FIG. 4 is a block diagram illustrating a geometric configuration of the medical device 100 with respect to the heart 102 according to one example. In the example shown, the medical device 100 has electrical leads **120*a* and 120*b* implanted into the heart 102 to apply stimulus signals to different areas of the heart 102, e.g., to achieve defibrillation, PFA treatment, and/or pacing. The electrical lead 120*a* is placed in the right ventricle of the heart 102. The electrical lead 120*b* is placed in the right atrium of the heart 102**.

The distal portion of the electrical lead **120*a* includes a tip electrode 402, a ring electrode 404, a coil electrode 406, and a PFA electrode 408. In the example shown, a fixation mechanism used in the electrical lead 120*a* is a passive-fixation mechanism, wherein one or more tines 412, e.g., constructed of an outer insulation material of the electrical lead 120*a*, are configured to facilitate advancement of the electrical lead 120*a* forward but hinder its retraction by engaging myocardial trabeculae in the right ventricle of the heart 102**. In another example, an active fixation mechanism, e.g., including an extendable/retractable helix screwed directly into the myocardium, is similarly used.

In some examples, the tip electrode 402 and the ring electrode 404 are used with the pacemaker modality of the circuit 300, with the tip electrode 402 typically operating as a cathode, and the ring electrode 404 typically operating as an anode. When the circuit 300 applies a suitably selected voltage between the electrodes 402 and 404, the resulting electrical current depolarizes the myocardium and triggers an action potential that spreads through the myocardium, thereby pacing the heart 102 accordingly. The electrodes 402 and 404 are also used as sensing electrodes. Sensing is the ability of the medical device 100 to detect the intrinsic cardiac activity. The cardiac signals picked up by the electrodes 402 and 404 in the sensing mode are detected and measured using the sensing circuit 370 (FIG. 3). In some examples in which the circuit 300 does not support the pacemaker modality, the electrodes 402 and 404 are used exclusively for sensing the intrinsic cardiac activity of the heart 102.

The coil electrode 406 is typically used with the defibrillator modality of the circuit 300. In some examples, the coil electrode 406 includes two separately switchable coils, referred to as the proximal coil and the distal coil, respectively. In such examples, the ring electrode 404 is typically absent. Circuit 300 operates to pace and sense between the tip electrode 402 and the distal coil of the coil electrode 406. Circuit 300 further operates to use both the distal and proximal coils of the coil electrode 406 for defibrillation, with the proximal coil of the coil electrode 406 being electrically connected to effectively increase the surface area of the coil electrode for better transduction of defibrillation pulses.

In the example shown, the PFA electrode 408 has a shape of a collar and is positioned in close proximity to a sinoatrial node 418 of the heart 102. In some other examples, the PFA electrode 408 is a ring electrode, includes multiple ring electrodes, or is a part (e.g., the distal coil) of the coil electrode 406. In the PFA modality of the circuit 300, a train of PFA pulses applied between the PFA electrode 408 and the box electrode 390 causes an electrical current 430 to flow therebetween, with at least a part of the electrical current 430 passing through the tissue surrounding the sinoatrial node 418.

In some examples, the electrical lead **120*b* includes a tip electrode 422 and a ring electrode 424 but does not include a defibrillation coil. The tip electrode 422 and the ring electrode 424 are generally analogous to the tip electrode 402 and the ring electrode 404, respectively, and are used for pacing and sensing, e.g., as indicated above. In some examples, a cardiac resynchronization therapy (CRT) ICD 100 also includes a third electrical lead 120 (not explicitly shown in FIG. 4**) placed into the coronary sinus and operated as a pacing lead.

FIG. 5 is a block diagram illustrating a geometric configuration of the medical device 100 with respect to the heart 102 according to another example. Similar to the example illustrated in FIG. 4, the electrical leads 120*a* and 120*b* are placed in the right ventricle and the right atrium, respectively, of the heart 102. The distal portion of the electrical lead 120*a* includes the tip electrode 402, the ring electrode 404, the coil electrode 406, and the PFA electrode 408. However, in the geometric configuration of FIG. 5, the PFA electrode 408 is placed near an atrioventricular node 518 of the heart 102. In the PFA modality of the circuit 300, a train of PFA pulses applied between the PFA electrode 408 and the box electrode 390 causes an electrical current 530 to flow therebetween, with at least a part of the electrical current 530 passing through the tissue surrounding the atrioventricular node 518. The distal portion of the electrical lead 120*b* includes the tip electrode 422 and the ring electrode 424.

Figure 6:
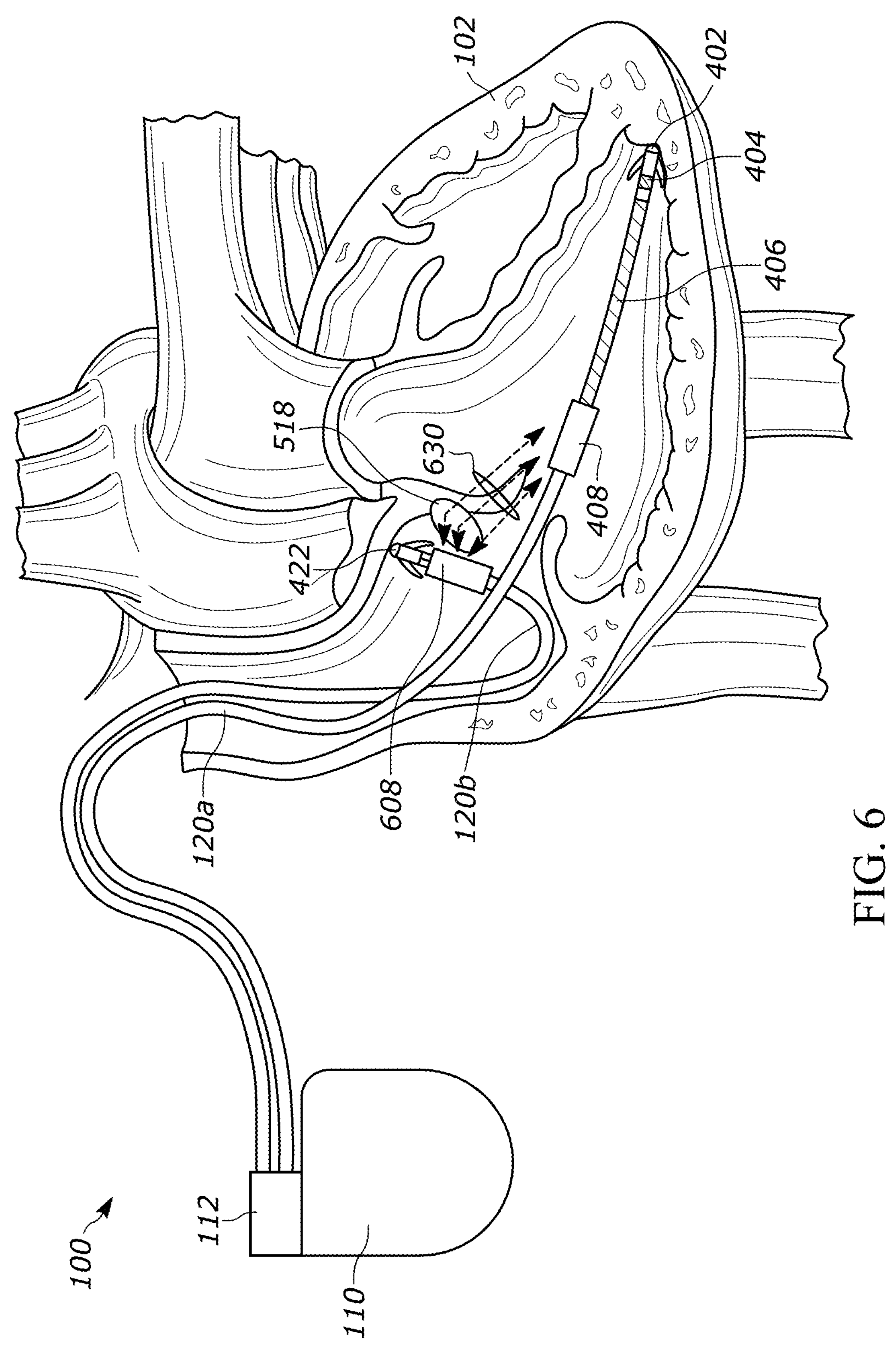
FIG. 6 is a block diagram illustrating a geometric configuration of the implantable medical device of FIG. 1 with respect to the patient heart according to yet another example.

FIG. 6 is a block diagram illustrating a geometric configuration of the medical device 100 with respect to the heart 102 according to yet another example. The electrical leads 120*a* and 120*b* are placed in the right ventricle and the right atrium, respectively, of the heart 102. The distal portion of the electrical lead 120*a* includes the tip electrode 402, the ring electrode 404, the coil electrode 406, and the PFA electrode 408. The PFA electrode 408 is placed near the atrioventricular node 518 of the heart 102. The distal portion of the electrical lead 120*b* includes the tip electrode 422 and a PFA electrode 608. The PFA electrode 608 is generally similar to the PFA electrode 408 and is also placed near the atrioventricular node 518 of the heart 102. In the PFA modality of the circuit 300, a train of PFA pulses applied between the PFA electrodes 408 and 608 causes an electrical current 630 to flow therebetween, with at least a part of the electrical current 630 passing through the tissue surrounding the atrioventricular node 518.

FIG. 7 is a block diagram illustrating a geometric configuration of the medical device 100 with respect to the heart 102 according to yet another example. The electrical leads 120*a* and 120*b* are placed in the right ventricle and the right atrium, respectively, of the heart 102. The distal portion of the electrical lead 120*a* includes the tip electrode 402, the ring electrode 404, the coil electrode 406, and the PFA electrode 408. In the geometric configuration of FIG. 7, the PFA electrode 408 is placed near an area 718 of the heart 102 where premature ventricular contractions (PVC) take place. In the PFA modality of the circuit 300, a train of PFA pulses applied between the PFA electrode 408 and the box electrode 390 causes an electrical current 730 to flow therebetween, with at least a part of the electrical current 730 passing through the tissue surrounding the PVC area 718. The distal portion of the electrical lead 120*b* includes the tip electrode 422 and the ring electrode 424.

In various examples, a suitable number of PFA electrodes, e.g., similar to the PFA electrodes 408, 608, is positioned on or within the heart 102 at locations where arrythmia signals can be blocked by post-implantation PFA treatment. In some instances, such PFA electrodes are placed at locations in anticipation of future ablation targets or in regions where arrhythmia recurrence is suspected. In some cases, the PFA electrodes are connected to the circuit 300 via one or more conductors that are separate from the electrical leads 120*a*, 120*b*. In general, the path of PFA energy delivery, such as that corresponding to the currents 430, 530, 630, 730, is chosen to encompass the tissue targeted for ablation therapy.

In some examples, the placement of the PFA electrodes (e.g., 408, 608) is based on an electrophysiological (EP) study. EP studies are tests that help doctors understand the nature of abnormal heart rhythms. An EP study may include combination and variation of a pacing signal, drugs, and other suitable means directed at discovering regions at which to place the PFA electrodes (e.g., 408, 608). An EP study may also include determining a variability in the cell structure due to disease, accident or genetic mutations, and changes from the native sinus rhythm (NSR). Example steps of an EP study typically include running one or more diagnostic protocols to ascertain the location and nature of a beneficial PFA intervention, determining a location for the PFA electrodes, and/or collecting confirmation diagnostics.

Various embodiments and geometric configurations of the medical device 100, including but not limited to the embodiments and geometric configurations described above in reference to FIGS. 1-7, beneficially enable, e.g., delivery of defibrillation and PFA therapy without having to insert new electrodes for the PFA therapy in a patient 101 already having an implanted defibrillator. For example, at the time of the implantation of medical device 100 and its electrical leads 120, the PFA electrodes (e.g., 408, 608) thereof are placed in the areas where a need for future ablation therapy is likely. As illustrated in FIGS. 4-7, the PFA electrodes can be placed on or affixed to one or more of the electrical leads 120. Various selectable energy delivery paths between various combinations of the PFA electrodes and/or the box electrodes 390 also beneficially provide significant flexibility in terms of the tissues that can be targeted. For example, the energy delivery path between the PFA electrode 408 and the box electrode 390 will create a different PFA treatment than the energy delivery path between the PFA electrodes 408 and 608.

Figure 8:
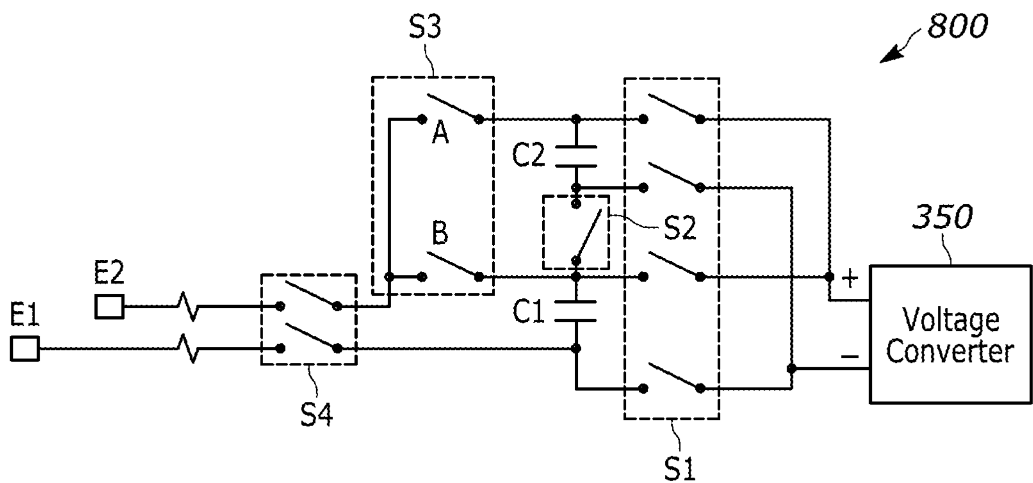
FIG. 8 is a block diagram illustrating a power circuit used in the implantable medical device of FIG. 1 according to one example.

FIG. 8 is a block diagram illustrating a power circuit 800 used in the medical device 100 according to one example. The power circuit 800 is configured to apply various voltages to electrodes E1 and E2 and includes the voltage converter 350, capacitive elements C1, C2 of the capacitor 304, and switches S1, S2, S3, S4 of the switching circuit 360 (also see FIG. 3). The switch S1 is used to connect the capacitors C1 and C2 to the voltage converter 350 for charging. During charging, the switches S2 and S3 are in the open state. After the capacitors C1 and C2 are charged, the switch S1 is switched from the closed state to the open state to disconnect the capacitors from the voltage converter 350. When the switch S2 is in the closed state, the capacitors C1, C2 are serially connected to one another, which causes the total voltage across the capacitor series to be a sum V1+V2 of the individual voltages V1, V2 of the capacitors C1, C2, respectively. The switches S2, S3 are used to select the voltage applied to the switch S4. For example, when the switch S2 is in the open state and branches A and B of the switch S3 are in the open state and closed state, respectively, the switch S4 receives the voltage V1. On the other hand, when the switch S2 is in the closed state and branches A and B of the switch S3 are in the closed state and open state, respectively, the switch S4 receives the voltage V1+V2. In some examples, the voltage V1 is suitable for defibrillation whereas the voltage V1+V2 is suitable for a PFA treatment. In some examples of the power circuit 800, more than two capacitive elements of the capacitor 304 are configured to be connectable in a series to provide a choice of more than two voltages for application to the switch S4.

The switch S4 is a selector switch configured to select the electrodes E1 and E2 from a plurality of electrodes of the medical device 100. According to various above-described examples, the plurality of electrodes of the medical device 100 includes at least a subset of the electrodes 390, 402, 404, 406, 408, 422, 424, and 608. In various additional examples, the plurality of electrodes of the medical device 100 includes other suitable sets of variously configured electrodes. For example, for the configuration illustrated in FIG. 4, 5, or 7, for the PFA modality, the electrodes E1 and E2 selected using the switch S4 are the electrodes 408 and 390, respectively. In another example, for the configuration illustrated in FIG. 6, for the PFA modality, the electrodes E1 and E2 selected using the switch S4 are the electrodes 408 and 608, respectively. In some examples, for the defibrillator modality, the electrodes E1 and E2 selected using the switch S4 are the electrodes 406 and 390, respectively.

Figure 9:
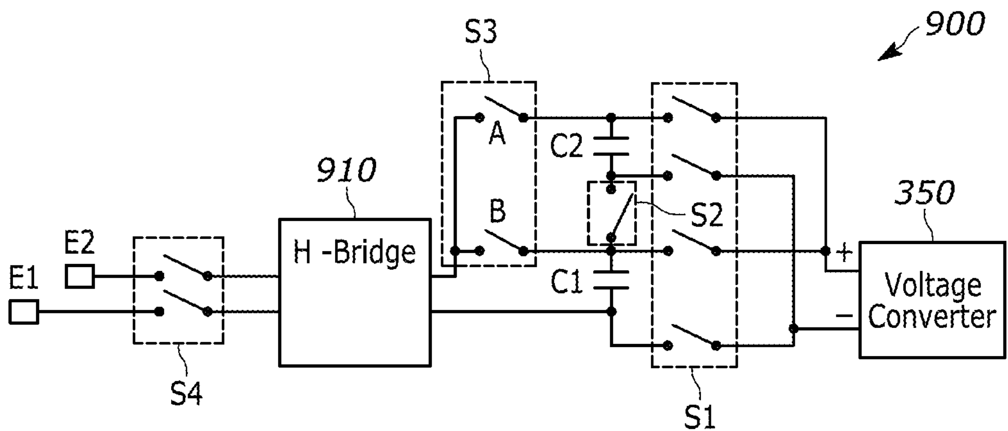
FIG. 9 is a block diagram illustrating a power circuit used in the implantable medical device of FIG. 1 according to another example.

FIG. 9 is a block diagram illustrating a power circuit 900 used in the medical device 100 according to another example. The power circuit 900 represents a modification of the power circuit 800 (FIG. 8). More specifically, the circuit 900 additionally includes an H-bridge circuit 910 inserted at the input of the switch S4. In an example implementation, the H-bridge circuit 910 includes four field-effect transistors (FETs) arranged in an H-shaped circuit configuration. For a fixed polarity of the input signal applied to the input port of the H-bridge circuit 910, the polarity of the output signal produced at the output port of the H-bridge circuit 910 alternates when the four FETs are switched OFF and ON pairwise. Other H-bridge implementations known to persons of ordinary skill in the pertinent art can similarly be used. Due to the presence of the H-bridge circuit 910, the circuit 900 is capable of generating biphasic waveforms for being applied to the electrodes E1, E2.

In various examples, the power circuits 800, 900 are reconfigurable by the electronic controller 330 to support different modalities for delivering a desired type of therapy, e.g., selected from the group consisting of defibrillation therapy, pacing therapy, and ablation therapy. The type of therapy delivered depends on the program applied by the electronic controller 330 to control the configurations of the switches S1-S4. Additionally, the power circuit 900 allows for biphasic waveform delivery.

Figure 10A:
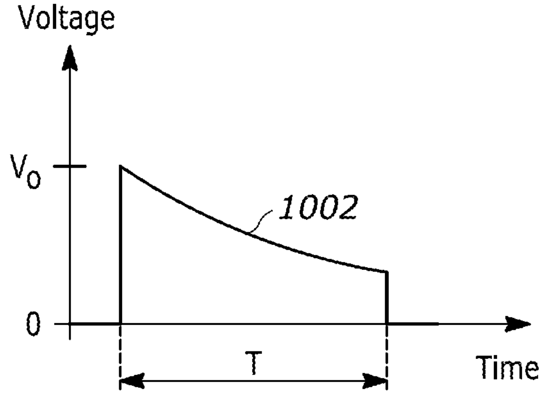
FIGS. 10A-10B are graphs illustrating waveforms generated with the power circuits of FIGS. 8-9 according to some examples.
Figure 10B:
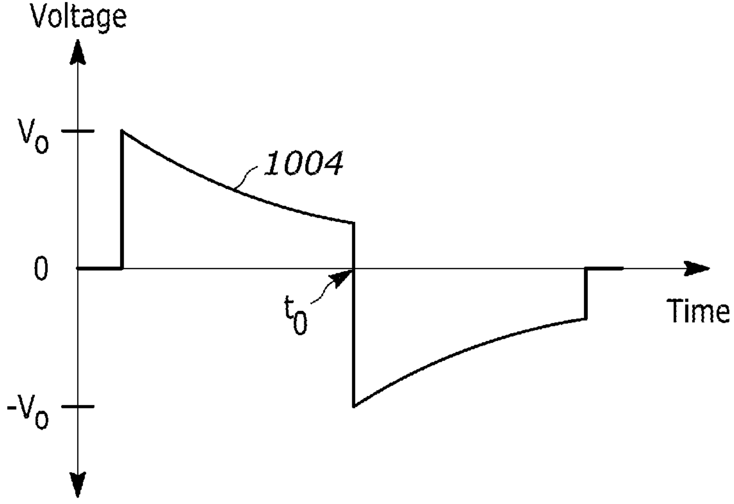

FIGS. 10A-10B illustrate waveforms 1002 and 1004 generated with the power circuits 800, 900 according to some examples. For example, the waveform 1002 (FIG. 10A) is a monophasic waveform of a positive polarity. The waveform 1002 can be generated using the power circuit 800 or the power circuit 900. The waveform 1004 (FIG. 10B) is a biphasic waveform in which the polarity changes from the positive polarity to the negative polarity at time to. The waveform 1004 can be generated using the power circuit 900. In some examples, various waveforms qualitatively similar to the waveforms 1002 and 1004 are used for different modalities of the medical device. For example, for the pacing modality, the peak voltage $V_0$ is typically lower than 10 V, and the pulse width T is approximately 2 ms. For the defibrillation modality, the voltage $V_0$ and the pulse width T are selected so that the delivered energy is in the range between about 34 and 40 Joules.

Figure 11:
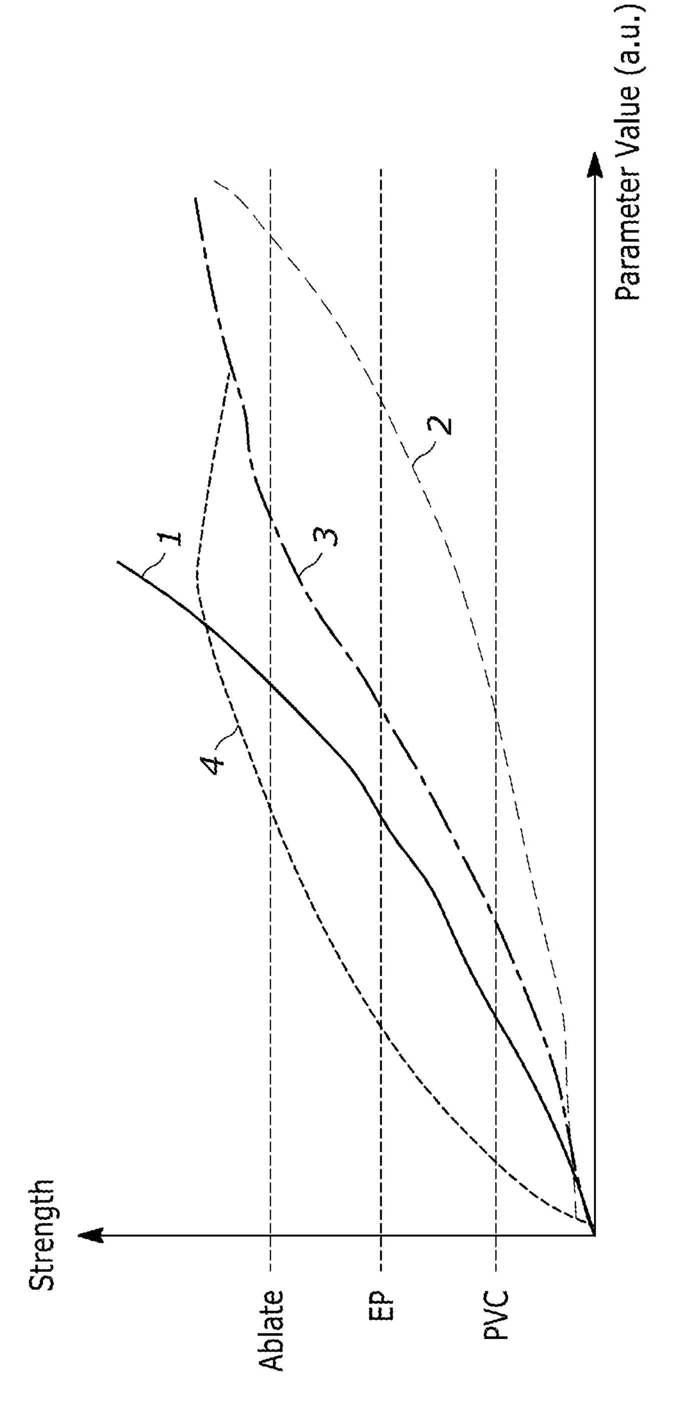
FIG. 11 is a graph illustrating selection of operating parameters for programming the implantable medical device of FIG. 1 according to some examples.

FIG. 11 is a graph illustrating selection of operating parameters for programming the medical device 100 according to some examples. The operating parameters include, but are not limited to, voltage, pulse width, pulse count, and pulse-repetition frequency. The vertical axis in FIG. 11 represents the relative strength of the ablation treatment, wherein irreversible ablation is a relatively strong (upper level) treatment, reversible electroporation is an intermediate-strength (middle level) treatment, and the PVC treatment is a relatively mild (lower level) treatment. Intersection points of the treatment levels with parametric curves 1, 2, 3, 4 of the medical device 100 provide the respective parameter values.

For example, the electric field between the electrodes E1, E2 is approximately inversely proportional to the distance between the two electrodes and is approximately directly proportional to the applied voltage. When the electrodes E1, E2 are separated by 1 millimeter (mm) with an applied voltage across the two electrodes being 100 V, the corresponding electric field is 100 V/mm. When the same voltage (100 V) is applied to the electrodes E1, E2 separated by twice the distance (2 mm), the electric field is 50 V/mm. This example illustrates that the position and combination of the electrodes and the voltage applied thereto are selected to achieve a desired strength of treatment quantified in terms of the electric field.

For a wide range of electroporation therapies, pulses on the order of 1-200 microseconds in duration and having amplitudes of 100-3000 volts are typically used. The voltage amplitude is usually lower for reversible electroporation or drug delivery and higher for irreversible electroporation. Also, the voltage applied to a pair of electrodes typically needs to be doubled when the distance between the electrodes is doubled, to induce approximately the same electric field strength between the electrodes. For defibrillation, the applied energy is typically in the range of 5 to 50 Joules with a pulse duration on the order of milliseconds. For pacing, an applied voltage is in the range of 0.1 V to 10 V with a pulse duration in the range of 0.5 to 2 milliseconds.

Figure 12:
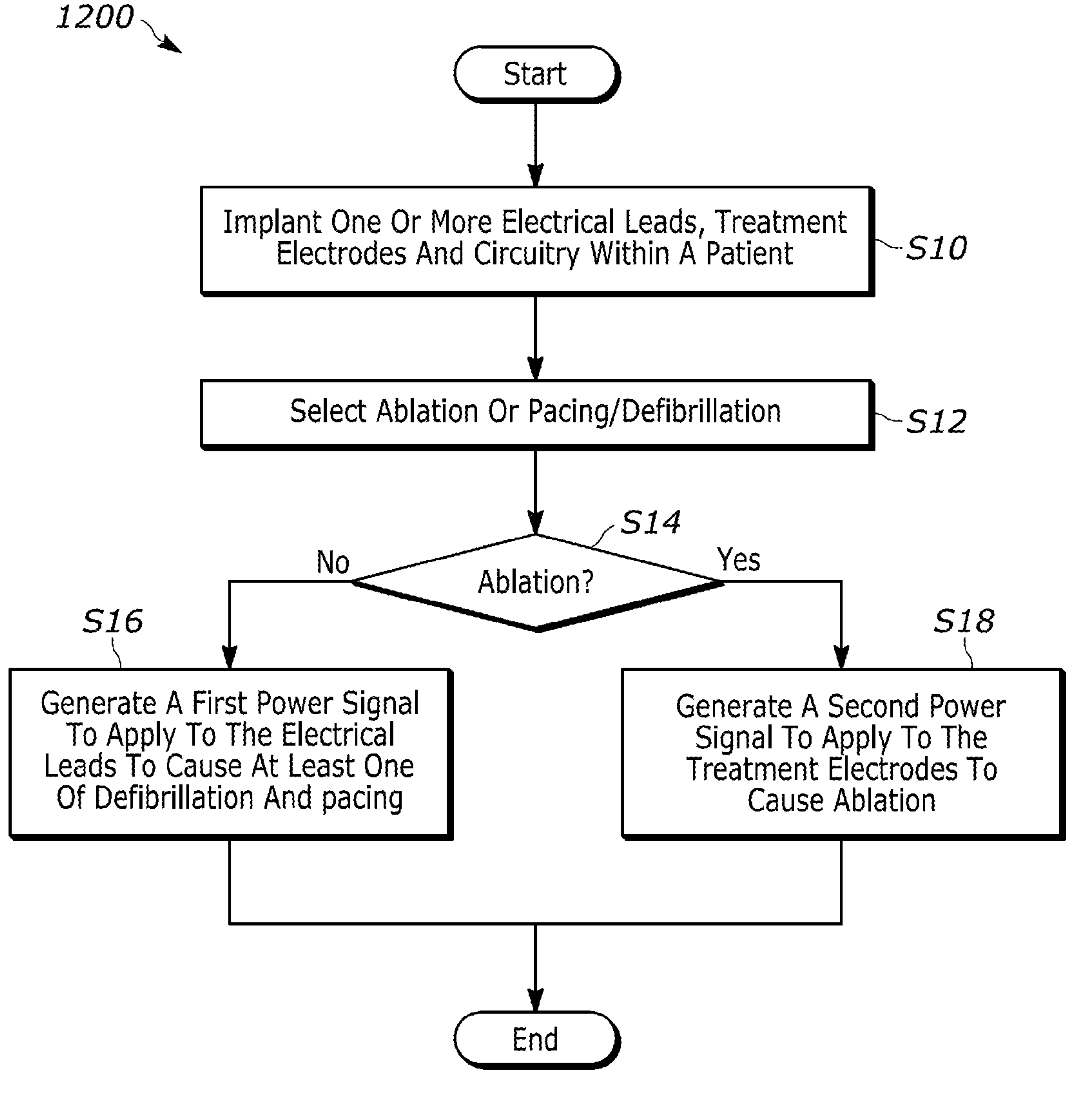
FIG. 12 is a flowchart illustrating a method of operating the implantable medical device of FIG. 1 according to some examples.

FIG. 12 is a flowchart illustrating a method 1200 of operating the medical device 100 according to some examples. The method 1200 includes implanting the medical device 100 into the patient 101 (Block S10). Example implantation geometries are described above in reference to FIGS. 1 and 4-7. The implanted medical device 100 is programmed, e.g., as described in reference to FIG. 2, with a selection of which therapy to apply, e.g., ablation or pacing/defibrillating (Block S12). When defibrillation or pacing is selected ("No" at Block S14), the method 1200 includes generating a first power signal to apply to the electrical leads 120 to cause at least one of defibrillation and pacing (Block S16). When ablation is selected ("Yes" at Block S14), the method 1200 includes generating a second power signal to apply to the treatment electrodes, e.g., 390, 408, 608, to cause ablation (Block S18).

According to one example disclosed above, e.g., in the summary section and/or in reference to any one or any combination of some or all of FIGS. 1-12, provided is an active implantable medical device, comprising: a plurality of electrodes including a first electrode and a second electrode; an electrical circuit in an interior portion of an implantable device box, the electrical circuit being electrically connectable to the plurality of electrodes to apply thereto electrical pulses according to a first modality and according to a different second modality; and a first electrical lead having a proximal end connectable to the electrical circuit and further having a distal portion implantable into a heart, the distal portion including the first electrode and the second electrode, wherein the electrical circuit is configured to apply a defibrillation pulse to the first electrode in the first modality and to apply an ablation pulse to the second electrode in the different second modality, the defibrillation pulse and the ablation pulse being different in at least one of a pulse amplitude and a pulse width.

In some examples of the above active implantable medical device, the electrical circuit comprises: a battery to provide a power supply voltage to at least a portion of the electrical circuit; a voltage converter to convert the power supply voltage into a higher voltage, the higher voltage having a magnitude that is at least 50 times larger than a magnitude of the power supply voltage; and a capacitor to be charged with the voltage converter.

In some examples of any of the above active implantable medical devices, the electrical circuit further comprises a switching circuit configured to apply a charged voltage of the capacitor between a selected pair of the plurality of electrodes.

In some examples of any of the above active implantable medical devices, the electrical circuit further comprises an electronic controller to control the switching circuit to cause the charged voltage to have a first voltage value for the first modality and to have a different second voltage value for the second modality.

In some examples of any of the above active implantable medical devices, the electrical circuit further comprises an electronic controller to control the switching circuit to change the selected pair.

In some examples of any of the above active implantable medical devices, the electrical circuit further comprises a wireless transceiver; and wherein the electronic controller is programmable with a program code received via the wireless transceiver, the program code having encoded therein instructions for controlling the switching circuit.

In some examples of any of the above active implantable medical devices, the plurality of electrodes includes a third electrode along an exterior surface of the device box; and wherein the selected pair in the different second modality includes the second electrode and the third electrode.

In some examples of any of the above active implantable medical devices, the device further comprises a second electrical lead having a proximal part connectable to the electrical circuit and a distal part implantable into the heart, the distal part including a third electrode of the plurality of electrodes, wherein the selected pair in the different second modality includes the second electrode and the third electrode.

In some examples of any of the above active implantable medical devices, the second electrode is placeable within the heart to drive an electrical current through a sinoatrial node of the heart, an atrioventricular node of the heart, or a premature ventricular contraction area of the heart.

In some examples of any of the above active implantable medical devices, the electrical circuit includes an H-bridge switchable to cause at least one of the defibrillation pulse and the ablation pulse to have a biphasic waveform.

In some examples of any of the above active implantable medical devices, the distal portion includes a third electrode; and wherein the electrical circuit includes a sensing circuit configured to sense a cardiac activity of the heart using the third electrode.

In some examples of any of the above active implantable medical devices, the distal portion includes a third electrode; and wherein the electrical circuit is configured to apply a pacing pulse to the third electrode in a third modality, the third modality being different both from the first modality and from the different second modality.

According to another example disclosed above, e.g., in the summary section and/or in reference to any one or any combination of some or all of FIGS. 1-12, provided is a medical system, comprising: an active implantable medical device including a first wireless transceiver; a programmer head including a second wireless transceiver, the first wireless transceiver and the second wireless transceiver being configured to wirelessly transmit data therebetween; and an electronic programmer connected to the programmer head, wherein the active implantable medical device comprises: a plurality of electrodes including a first electrode and a second electrode; an electrical circuit in an interior portion of an implantable device box, the electrical circuit being electrically connectable to the plurality of electrodes to apply thereto electrical pulses according to a first modality and according to a different second modality; and a first electrical lead having a proximal end connectable to the electrical circuit and further having a distal portion implantable into a heart, the distal portion including the first electrode and the second electrode; and wherein the electrical circuit is configured to apply a defibrillation pulse to the first electrode in the first modality and to apply an ablation pulse to the second electrode in the different second modality, the defibrillation pulse and the ablation pulse being different in at least one of a pulse amplitude and a pulse width.

In some examples of the above medical system, the electrical circuit comprises an electronic controller programmable from the electronic programmer using the data transmitted between the first wireless transceiver and the second wireless transceiver.

In some examples of any of the above medical systems, the electrical circuit comprises: a battery to provide a power supply voltage to at least a portion of the electrical circuit; a voltage converter to convert the power supply voltage into a higher voltage, the higher voltage having a magnitude that is at least 50 times larger than a magnitude of the power supply voltage; and a capacitor to be charged with the voltage converter.

In some examples of any of the above medical systems, the electrical circuit further comprises a switching circuit configured to apply a charged voltage of the capacitor between a selected pair of the plurality of electrodes.

In some examples of any of the above medical systems, the plurality of electrodes includes a third electrode along an exterior surface of the device box; and wherein the selected pair in the different second modality includes the second electrode and the third electrode.

In some examples of any of the above medical systems, the active implantable medical device further comprises a second electrical lead having a proximal part connectable to the electrical circuit and a distal part implantable into the heart, the distal part including a third electrode of the plurality of electrodes; and wherein the selected pair in the different second modality includes the second electrode and the third electrode.

In some examples of any of the above medical systems, the second electrode is placeable within the heart to drive an electrical current through a sinoatrial node of the heart, an atrioventricular node of the heart, or a premature ventricular contraction area of the heart.

In some examples of any of the above medical systems, the distal portion includes a third electrode; and wherein the electrical circuit includes a sensing circuit configured to sense a cardiac activity of the heart using the third electrode.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

Unless explicitly stated otherwise, each numerical value and range should be interpreted as being approximate as if the word "about" or "approximately" preceded the value or range.

The use of figure numbers and/or figure reference labels (if any) in the claims is intended to identify one or more possible embodiments of the claimed subject matter in order to facilitate the interpretation of the claims. Such use is not to be construed as necessarily limiting the scope of those claims to the embodiments shown in the corresponding figures.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Reference herein to "one embodiment" or "an embodiment" means that a particular feature, structure, or characteristic described in connection with the embodiment can be included in at least one embodiment of the disclosure. The appearances of the phrase "in one embodiment" in various places in the specification are not necessarily all referring to the same embodiment, nor are separate or alternative embodiments necessarily mutually exclusive of other embodiments. The same applies to the term "implementation."

Unless otherwise specified herein, the use of the ordinal adjectives "first," "second," "third," etc., to refer to an object of a plurality of like objects merely indicates that different instances of such like objects are being referred to, and is not intended to imply that the like objects so referred-to have to be in a corresponding order or sequence, either temporally, spatially, in ranking, or in any other manner.

Unless otherwise specified herein, in addition to its plain meaning, the conjunction "if" may also or alternatively be construed to mean "when" or "upon" or "in response to determining" or "in response to detecting," which construal may depend on the corresponding specific context. For example, the phrase "if it is determined" or "if [a stated condition] is detected" may be construed to mean "upon determining" or "in response to determining" or "upon detecting [the stated condition or event]" or "in response to detecting [the stated condition or event]."

Also, for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements. The same type of distinction applies to the use of terms "attached" and "directly attached," as applied to a description of a physical structure. For example, a relatively thin layer of adhesive or other suitable binder can be used to implement such "direct attachment" of the two corresponding components in such physical structure.

The described embodiments are to be considered in all respects as only illustrative and not restrictive. In particular, the scope of the disclosure is indicated by the appended claims rather than by the description and figures herein. All changes that come within the meaning and range of equivalency of the claims are to be embraced within their scope.

The functions of the various elements shown in the figures, including any functional blocks labeled as "processors" and/or "controllers," may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and nonvolatile storage. Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

As used in this application, the term "circuitry" may refer to one or more or all of the following: (a) hardware-only circuit implementations (such as implementations in only analog and/or digital circuitry); (b) combinations of hardware circuits and software, such as (as applicable): (i) a combination of analog and/or digital hardware circuit(s) with software/firmware and (ii) any portions of hardware processor(s) with software (including digital signal processor(s)), software, and memory(ies) that work together to cause an apparatus, such as a mobile phone or server, to perform various functions); and (c) hardware circuit(s) and or processor(s), such as a microprocessor(s) or a portion of a microprocessor(s), that requires software (e.g., firmware) for operation, but the software may not be present when it is not needed for operation." This definition of circuitry applies to all uses of this term in this application, including in any claims. As a further example, as used in this application, the term circuitry also covers an implementation of merely a hardware circuit or processor (or multiple processors) or portion of a hardware circuit or processor and its (or their) accompanying software and/or firmware. The term circuitry also covers, for example and if applicable to the particular claim element, a baseband integrated circuit or processor integrated circuit for a mobile device or a similar integrated circuit in server, a cellular network device, or other computing or network device.

It should be appreciated by those of ordinary skill in the art that any block diagrams herein represent conceptual views of illustrative circuitry embodying the principles of the disclosure. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

What is claimed is:

1. An active implantable medical device, comprising:

a plurality of electrodes including a first electrode, a second electrode, and a third electrode;

an implantable device box configured to be implanted into a pocket of a patient body outside the heart, wherein the third electrode is along an exterior surface of the device box;

an electrical circuit in an interior portion of the implantable device box, the electrical circuit being electrically connectable to the plurality of electrodes to apply thereto electrical pulses according to a first modality and according to a different second modality; and a first electrical lead having a proximal end connectable to the electrical circuit and further having a distal portion implantable into a heart, the distal portion including the first electrode and the second electrode, wherein the electrical circuit is configured to apply a defibrillation pulse to the first electrode in the first modality and to apply an ablation pulse between the second electrode and the third electrode in the different second modality, the defibrillation pulse and the ablation pulse being different in at least one of a pulse amplitude and a pulse width; and wherein the second and third electrodes are configured to cause an electrical current to pass through tissue targeted for ablation therapy, the tissue being selected from the group consisting of a sinoatrial node of the heart, an atrioventricular node of the heart, and a premature ventricular contraction area of the heart.

2. The active implantable medical device of claim 1, wherein the electrical circuit comprises:

a battery to provide a power supply voltage to at least a portion of the electrical circuit;

a voltage converter to convert the power supply voltage into a higher voltage, the higher voltage having a magnitude that is at least 50 times larger than a magnitude of the power supply voltage; and a capacitor to be charged with the voltage converter.

3. The active implantable medical device of claim 2, wherein the electrical circuit further comprises a switching circuit configured to apply a charged voltage of the capacitor between a selected pair of the plurality of electrodes.

4. The active implantable medical device of claim 3, wherein the electrical circuit further comprises an electronic controller to control the switching circuit to cause the charged voltage to have a first voltage value for the first modality and to have a different second voltage value for the second modality.

5. The active implantable medical device of claim 3, wherein the electrical circuit further comprises an electronic controller to control the switching circuit to change the selected pair.

6. The active implantable medical device of claim 5, wherein the electrical circuit further comprises a wireless transceiver; and wherein the electronic controller is programable with a program code received via the wireless transceiver, the program code having encoded therein instructions for controlling the switching circuit.

7. The active implantable medical device of claim 1, further comprising a second electrical lead having a proximal part connectable to the electrical circuit and a distal part implantable into the heart, the distal part including a fourth electrode of the plurality of electrodes, wherein the different second modality includes ablation between the second electrode positioned in a first chamber of the heart and the fourth electrode positioned in a different second chamber of the heart.

8. The active implantable medical device of claim 1, wherein the second and third electrodes are configured to drive the electrical current through the atrioventricular node of the heart.

9. The active implantable medical device of claim 1, wherein the electrical circuit includes an H-bridge switchable to cause at least one of the defibrillation pulse and the ablation pulse to have a biphasic waveform.

10. The active implantable medical device of claim 1, wherein the distal portion includes a fourth electrode; and wherein the electrical circuit includes a sensing circuit configured to sense a cardiac activity of the heart using the fourth electrode.

11. The active implantable medical device of claim 1, wherein the distal portion includes a fourth electrode; and wherein the electrical circuit is configured to apply a pacing pulse to the fourth electrode in a third modality, the third modality being different both from the first modality and from the different second modality.

12. The active implantable medical device of claim 1, wherein the second and third electrodes are configured to drive the electrical current through the sinoatrial node of the heart.

13. The active implantable medical device of claim 1, wherein the second and third electrodes are configured to drive the electrical current through the premature ventricular contraction area of the heart.

14. A medical system, comprising:

an active implantable medical device including a first wireless transceiver;

a programmer head including a second wireless transceiver, the first wireless transceiver and the second wireless transceiver being configured to wirelessly transmit data therebetween; and an electronic programmer connected to the programmer head, wherein the active implantable medical device comprises:

a plurality of electrodes including a first electrode and a second electrode;

an implantable device box configured to be implanted into a pocket of a patient body outside the heart, wherein the third electrode is along an exterior surface of the device box;

an electrical circuit in an interior portion of the implantable device box, the electrical circuit being electrically connectable to the plurality of electrodes to apply thereto electrical pulses according to a first modality and according to a different second modality; and a first electrical lead having a proximal end connectable to the electrical circuit and further having a distal portion implantable into a heart, the distal portion including the first electrode and the second electrode; and wherein the electrical circuit is configured to apply a defibrillation pulse to the first electrode in the first modality and to apply an ablation pulse between the second electrode and the third electrode in the different second modality, the defibrillation pulse and the ablation pulse being different in at least one of a pulse amplitude and a pulse width; and wherein the second and third electrodes are configured to cause an electrical current to pass through tissue targeted for ablation therapy, the tissue being selected from the group consisting of a sinoatrial node of the heart, an atrioventricular node of the heart, and a premature ventricular contraction area of the heart.

15. The medical system of claim 14, wherein the electrical circuit comprises an electronic controller programmable from the electronic programmer using the data transmitted between the first wireless transceiver and the second wireless transceiver.

16. The medical system of claim 14, wherein the electrical circuit comprises:

a battery to provide a power supply voltage to at least a portion of the electrical circuit;

a voltage converter to convert the power supply voltage into a higher voltage, the higher voltage having a magnitude that is at least 50 times larger than a magnitude of the power supply voltage; and a capacitor to be charged with the voltage converter.

17. The medical system of claim 14, wherein the electrical circuit further comprises a switching circuit configured to apply a charged voltage of the capacitor between a selected pair of the plurality of electrodes.

18. The medical system of claim 14, wherein the active implantable medical device further comprises a second electrical lead having a proximal part connectable to the electrical circuit and a distal part implantable into the heart, the distal part including a fourth electrode of the plurality of electrodes; and wherein the different second modality includes ablation between the second electrode positioned in a first chamber of the heart and the fourth electrode positioned in a different second chamber of the heart.

19. The medical system of claim 14, wherein the second and third electrodes are configured to drive the electrical current through the atrioventricular node of the heart.

20. The medical system of claim 14, wherein the distal portion includes a fourth electrode; and wherein the electrical circuit includes a sensing circuit configured to sense a cardiac activity of the heart using the fourth electrode.

* * * * *